(12) United States Patent
LeSourd

(10) Patent No.: US 7,164,939 B2
(45) Date of Patent: Jan. 16, 2007

(54) DISPOSABLE BIOMEDICAL ELECTRODE HAVING MULTIPLE CONNECTION SITES

(75) Inventor: Bonnie Briny LeSourd, Pewaukee, WI (US)

(73) Assignee: The General Electric Company, Schenectady, NY (US)

( * ) Notice: Subject to any disclaimer, the term of this patent is extended or adjusted under 35 U.S.C. 154(b) by 161 days.

(21) Appl. No.: 10/955,002

(22) Filed: Sep. 23, 2004

(65) Prior Publication Data
US 2006/0063996 A1    Mar. 23, 2006

(51) Int. Cl.
*A61B 5/04* (2006.01)
(52) U.S. Cl. .................... 600/391; 600/392
(58) Field of Classification Search ............... 600/372, 600/382, 386, 391–393; 606/32; 607/149, 607/152, 153
See application file for complete search history.

(56) References Cited

U.S. PATENT DOCUMENTS

| 4,051,842 | A |  | 10/1977 | Hazel et al. |  |
| 4,524,087 | A |  | 6/1985 | Engel |  |
| 4,679,563 | A |  | 7/1987 | Wada et al. |  |
| 4,858,617 | A |  | 8/1989 | Sanders |  |
| 4,890,622 | A |  | 1/1990 | Ferrari |  |
| 5,012,810 | A |  | 5/1991 | Strand et al. |  |
| 5,191,887 | A | * | 3/1993 | Cartmell | 600/392 |
| 5,348,007 | A | * | 9/1994 | Hitti | 600/391 |
| 6,623,664 | B1 |  | 9/2003 | Takaki et al. |  |

FOREIGN PATENT DOCUMENTS

WO    WO-00/42904    7/2000

OTHER PUBLICATIONS

British Search Report, Nov. 21, 2005.

* cited by examiner

*Primary Examiner*—Lee S. Cohen
(74) *Attorney, Agent, or Firm*—Andrus, Sceales, Starke & Sawall, LLP

(57) ABSTRACT

A disposable biomedical electrode is triangular in shape with connection sites for a lead wire formed at the apexes of the triangular shape.

16 Claims, 2 Drawing Sheets

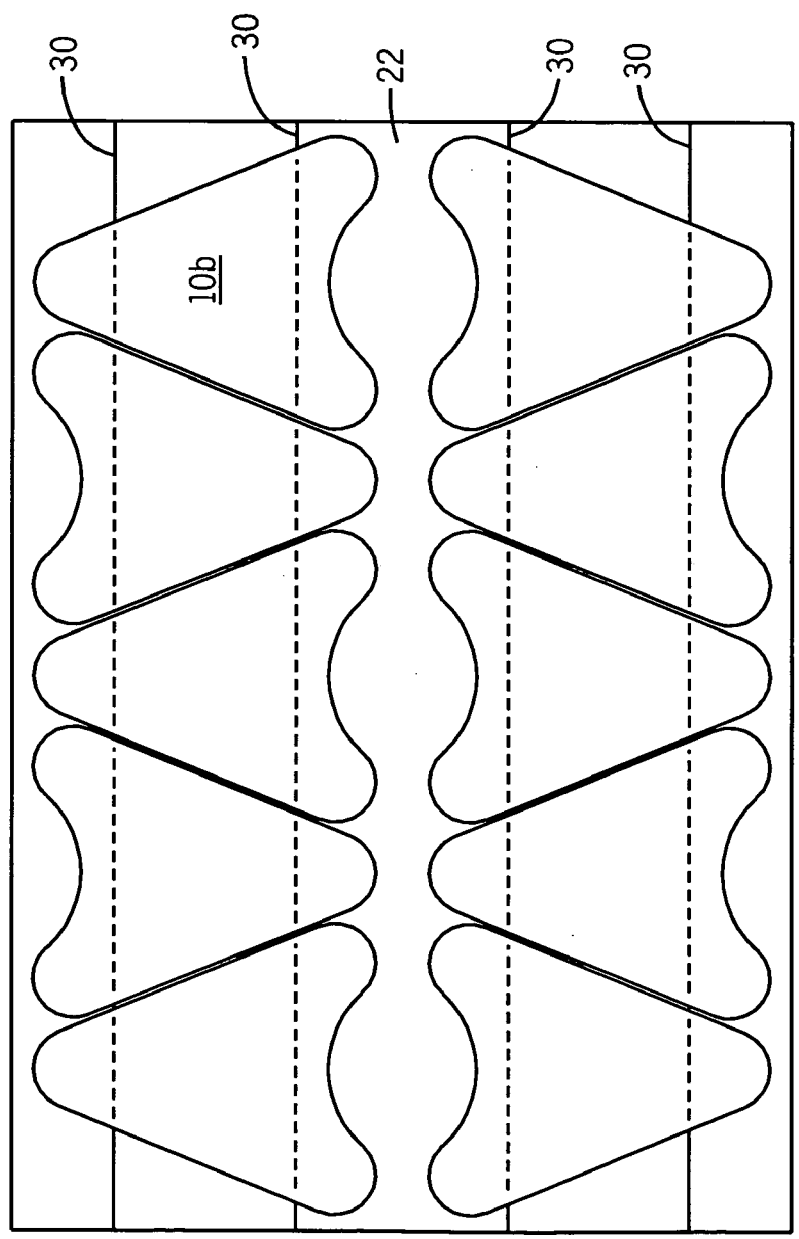

DISPOSABLE BIOMEDICAL ELECTRODE HAVING MULTIPLE CONNECTION SITES

FIELD OF THE INVENTION

The present invention relates to a disposable, biomedical electrode having multiple sites for connecting lead wires to the electrode. The biomedical electrode may be used to collect ECG potentials from the body of a patient.

BACKGROUND OF THE INVENTION

Electrocardiography (ECG) is a well established method of measuring the set of electrical events that are intrinsic to the heart's function. Electrocardiography has found applications in a wide variety of clinical situations including resting diagnostic procedures; surgical and emergency room procedures; cardiac care; critical care; ambulatory monitoring; stress diagnostic procedures; and in providing remote patient monitoring.

Biomedical electrodes are used to transmit ECG potentials from the body, via lead wires, to an electrocardiograph to record electrocardiographic signals. The lead wire connection to the electrocardiograph can be direct or indirect, as through telemetry equipment. Biomedical electrodes may be of the reusable type but for reasons of hygiene and economy are often of the disposable type.

A disposable biomedical electrode is typically composed of a conductive and adhesive layer attached to a conductive layer of an insulative substrate. The adhesive layer retains the electrode to the skin of the patient. A lead wire is attached to the conductive layer of the substrate by a lead clip, e.g. of the alligator type.

The current offering of disposable electrodes suffer from a limitation in that they typically provide only one connection site for the lead wire. This is usually via a tab on the periphery of a generally rectangular or circular electrode. This limitation requires the technician to devote additional time in properly positioning the electrode on the patient to ensure the availability of a connection point and restricts the patient's range of movement while attached to the lead wires. Proper electrode positioning is also required due to the shear stress applied to the electrode by the weight and angle of the lead wire. This stress acts on the adhesive layer, which may include a conductive gel, and causes the electrode to lift up or roll over from its position in contact with the patient's skin. Such an occurrence reduces not only the area in which the electrode is in contact with the skin but also the overall quality of the connection itself, thereby introducing error in the ECG measurement. In a worst case scenario, either the electrode or lead wire will detach due to the stress and angle of the lead wire, causing loss of the ECG signal. This requires repositioning or replacement of the electrode.

It is therefore desirable to provide an electrode that facilitates connection of the lead wire to the electrode and reduces the electrode's tendency to lift up or roll-over due to stresses exerted by the lead wire.

SUMMARY OF THE INVENTION

The present invention provides an improved, disposable biomedical electrode that provides multiple lead wire connection sites thereby allowing the technician to easily connect the lead wire to an optimal connection site for the position of both the electrode and the patient. Also provided is a structure by which manufacture, packaging, and use of the biomedical electrodes are made more efficient.

The disposable biomedical electrode of the present invention is triangular in shape so that lead wire connection sites may be located at the apexes of the triangle. The electrode may be formed of a triangular substrate that is conductive along a surface thereof. A conductive adhesive layer is applied to the conductive surface of the substrate for removably attaching the electrode to the skin of the patient. The apexes of the triangular substrate are exposed so that a lead wire may be clipped to the substrate in contact with the conductive surface to obtain the ECG or other biopotential signal from the patient.

BRIEF DESCRIPTION OF THE DRAWING

The drawings illustrate exemplary embodiments of the disposable biomedical electrode having multiple connection sites of the present invention.

FIG. 4 is a top view showing a plurality of electrodes on a release liner; and showing a further modification of the biomedical electrode; and FIG. 5 is a side view of the subject matter of FIG. 4.

DETAILED DESCRIPTION OF THE PREFERRED EMBODIMENT

Figure 1:
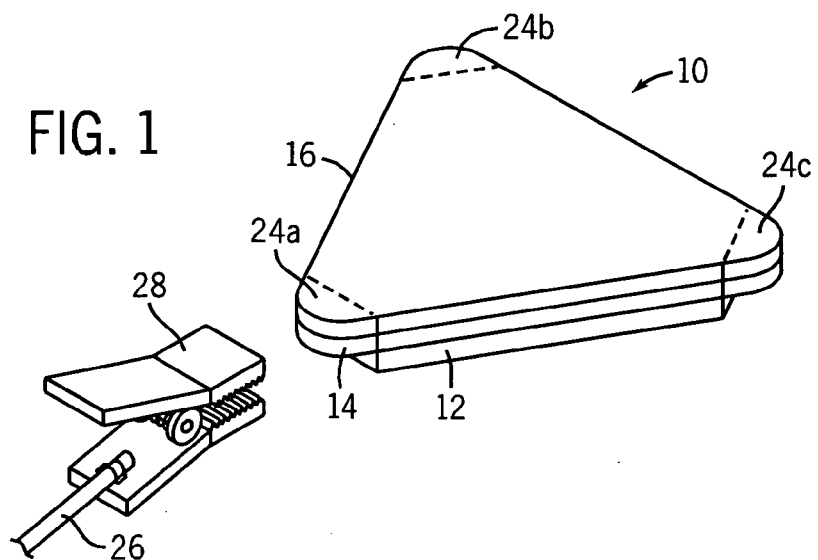
FIG. 1 is a perspective view of one embodiment of a biomedical electrode of the present invention.
Figure 2:
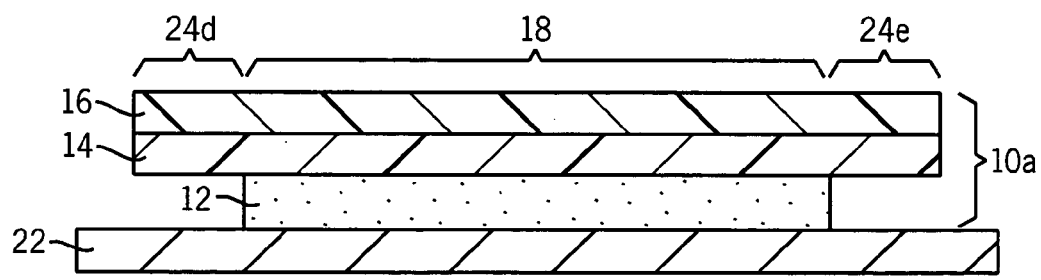
FIG. 2 is a cross-sectional view illustrating the components of the biomedical electrode of the present invention.

As shown in FIGS. 1 and 2, biomedical electrode 10 of the present invention comprises a conductive adhesive layer 12, a conductive layer 14, and an insulative substrate 16. Adhesive layer 12 is applied to the conductive layer 14. The adhesive layer 12 of the biomedical electrode 10 is protected until use by attachment to a suitable release liner 22 shown in FIGS. 4 and 5. While conductive layer 14 is shown as a separate layer in FIG. 1, it will be appreciated that it may be integrally formed with substrate 16 if desired so that substrate 16 is partially or completely conductive in nature. The layers and substrate of the electrode are flexible to allow the electrode to conform to the skin of the patient.

Figure 3:
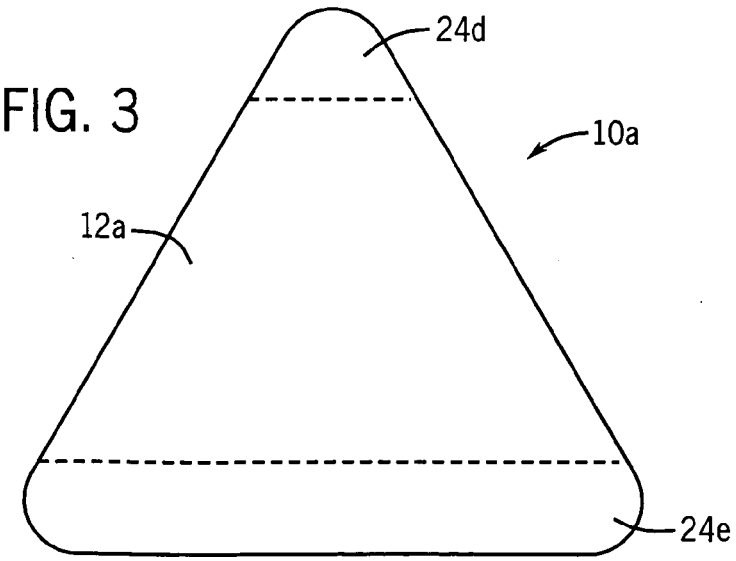
FIG. 3 is a top view of another embodiment of a biomedical electrode of the present invention.

Substrate 16 has a triangular shape with the shape of an equilateral triangle being shown in FIGS. 1 and 3. In a typical embodiment of the present invention, the electrode may be approximately one inch to one and a half inches on a side. If a separate layer, conductive layer 14 may be co-extensive with substrate 16. Adhesive layer 12 is formed as a truncated triangle to expose apexes 24*a*, 24*b*, and 24*c* of substrate 16 and conductive layer 14. Each of the apexes 24*a*, 24*b*, and 24*c* form a connection site for an electrode lead wire 26 having connection clip 28 which may be of the alligator type, thereby to provide multiple connection sites for the electrode.

FIG. 3 depicts a modification of the structure of the biomedical electrode of the present invention. Biomedical electrode 10*a* shown in FIG. 3 is triangular in shape while the adhesive layer 12 is trapezoidal in form and is attached to the approximately central ⅔rds of the biomedical electrode 10. The remaining portion of substrate 16 and conductive layer 14, disposed at the top and bottom of the adhesive layer 12, form the multiple connection sites 24*d* and 24*e* for the electrode. Thus, at the base of the triangular electrode 10*a*, two of the connection sites shown in FIG. 1 are, in effect, merged together.

FIG. 4 shows a modification of the electrode shown in FIG. 3 in which the electrode 106 is in the shape of an isosceles triangle and the apexes at the base of the triangle are more fully defined by curving the base.

To use biomedical electrode 10, 10*a*, 10*b*, it is removed from the release liner 22 and the conductive adhesive layer 12 secured to the desired location on the patient's body. The conductive adhesive layer 12 not only attaches the biomedical electrode 10 to the patient, but also facilitates the transmission of the biopotential signal from the patient to the electrode. The technician connects the lead wire clip 28 to whichever connection site 24 will provide the most reliable and convenient attachment point. With multiple options available for lead wire attachment, the technician may more quickly position the biomedical electrode on a patient, thus reducing the initial time spent by the technician. The need for subsequent repositioning or replacement of the biomedical electrode is also reduced.

In a preferred embodiment for manufacturing the biomedical electrodes of the invention, the electrodes may be die cut from a strip or sheet of substrate/conductive layer material and arranged as shown in FIG. 4 with the sides of the electrodes contiguous and the apex of one electrode next to the base of an adjacent electrode. The triangular shape of electrodes allows them to be die cut to the configuration shown in FIG. 4 with little material wastage or scrape.

A strip of conductive adhesive 12 is applied on the triangular substrates in the pattern shown in FIG. 4 so that the middle of the electrode contains the adhesive while both ends are free of adhesive. The electrodes are then placed on release liner 22. Or, the strip of conductive adhesive may be first applied to the liner and the substrate/conductive layer material applied to the adhesive. In either case the result is a positioning of electrode 10 on release liner 22 in a row or rows with the sides of the electrodes contiguous and the apex of one electrode adjacent the base of an adjacent electrode, as shown in FIG. 4. This simplification of the electrode manufacturing process results in greater time and cost efficiency in manufacturing the electrodes.

The electrodes 10, 10*a*, 10*b* are positioned on a release liner or release card 22 that is perforated or scored at lines 30 shown in FIG. 4 along the sides of the strip of adhesive. When the card is folded by the technician along a line 30 as shown in FIG. 5, the points of the triangular biomedical electrodes extend away from the liner so that the technician has simplified access to the connection sites of the electrodes. This increased access allows the technician to remove the electrodes from the release liner with greater ease, and prevents adhesive from getting on the technicians hands and interfering with the connection and use of the electrodes. Additionally, the increased access to the connection sites of the biomedical electrode will allow the technician to pre-attach the lead wire to the electrode before removing the electrode from the liner, thus creating greater efficiency in connecting the patient to an electrocardiograph or similar apparatus.

Various alternatives and embodiments are contemplated as being within the scope of the following claims, particularly pointing out and distinctly claiming the subject matter regarded as the invention. For example, while the invention has been described above in connection with obtaining ECG signals, it will be appreciated that it may be used to obtain other biopotential signals, such as electroencephalographic (EEG) signals or electromyographic (EMG) signals.

What is claimed is:

1. An improved disposable biomedical electrode, said electrode comprising:
    a sheet-like flexible electrode substrate, said substrate being electrically conductive along a surface thereof, and;
    an electrically conductive adhesive layer coupled to said conductive surface;
    said electrode so formed having a triangular configuration, the electrically conductive surface of the apexes of said electrode being exposed for forming multiple connection sites for a biopotential lead wire.

2. A biomedical electrode of claim 1 wherein said conductive adhesive layer is coupled to a central portion of said electrically conductive surface.

3. A biomedical electrode of claim 2 wherein said central portion is generally a central ⅔'s of said electrically conductive surface.

4. A biomedical electrode of claim 1 wherein three apexes of said electrode are exposed.

5. A biomedical electrode of claim 4 wherein the conductive adhesive layer is in the shape of a truncated triangle.

6. A biomedical electrode of claim 1 wherein an apex and a base of said electrode are exposed.

7. A biomedical electrode of claim 6 wherein the conductive adhesive layer is in the shape of a trapezoid.

8. A biomedical electrode of claim 7 wherein one of the sides of the triangular electrode is curved.

9. A biomedical electrode of claim 1 wherein one of the sides of the triangular electrode is curved.

10. A biomedical electrode of claim 1 wherein said electrode is removably adhered to a release liner proximate to said conductive adhesive layer, said release liner being bendable away from said electrode to free said connection sites from said release liner.

11. A biomedical electrode of claim 1 wherein said biomedical electrode is an ECG electrode.

12. A disposable biomedical electrode assembly comprising:
    a release liner: and
    a plurality of disposable biomedical electrodes removably adhered to said release liner, each electrode of the plurality comprising a sheet-like flexible electrode substrate, said substrate being electrically conductive along a surface thereof, and an electrically conductive adhesive layer coupled to said conductive surface, said electrodes so formed having a triangular configuration, the electrically conductive surface of the apexes of said electrodes being exposed for forming multiple connection sites for a biopotential lead wire.

13. A biomedical electrode assembly of claim 12 wherein said plurality of electrodes are arranged on said release liner with the sides of said triangularly shaped electrodes contiguous and a base of one electrode being next to an apex of an adjacent electrode.

14. A biomedical electrode assembly of claim 13 wherein said conductive adhesive layer is arranged in a strip across said adjacent electrodes.

15. A biomedical electrode assembly of claim 12 wherein said release liner is bendable away from the electrodes.

16. A biomedical electrode assembly of claim 12 wherein said biomedical electrodes are ECG electrodes.

\* \* \* \* \*